United States Patent [19]

Engelson

[11] Patent Number: 5,749,849
[45] Date of Patent: *May 12, 1998

[54] VARIABLE STIFFNESS BALLOON CATHETER

[75] Inventor: Erik T. Engelson, Menlo Park, Calif.

[73] Assignee: Target Therapeutics, Inc., Fremont, Calif.

[*] Notice: The term of this patent shall not extend beyond the expiration date of Pat. No. 5,437,632.

[21] Appl. No.: 557,075

[22] PCT Filed: May 20, 1994

[86] PCT No.: PCT/US94/05679

§ 371 Date: Aug. 12, 1996

§ 102(e) Date: Aug. 12, 1996

[87] PCT Pub. No.: WO94/27668

PCT Pub. Date: Dec. 8, 1994

Related U.S. Application Data

[63] Continuation-in-part of Ser. No. 71,284, Jun. 2, 1993, Pat. No. 5,437,632.

[51] Int. Cl.⁶ ............................................... A61M 31/00
[52] U.S. Cl. ................................................ 604/53; 604/96
[58] Field of Search .......................... 604/53, 93, 96, 604/264, 280; 606/191–194

[56] References Cited

U.S. PATENT DOCUMENTS

| | | |
|---|---|---|
| 4,739,768 | 4/1988 | Engelson . |
| 4,782,834 | 11/1988 | Maguire et al. . |
| 4,813,934 | 3/1989 | Engelson et al. . |
| 4,976,720 | 12/1990 | Machold et al. . |
| 5,047,045 | 9/1991 | Arney et al. . |
| 5,100,381 | 3/1992 | Burns . |
| 5,102,415 | 4/1992 | Guenther et al. ............ 606/159 |
| 5,171,221 | 12/1992 | Samson . |
| 5,188,635 | 2/1993 | Radtke ............ 606/14 |
| 5,192,290 | 3/1993 | Hilal ............ 606/159 |
| 5,437,632 | 8/1995 | Engelson . |

FOREIGN PATENT DOCUMENTS

| | | |
|---|---|---|
| 0437795 | 7/1991 | European Pat. Off. . |
| WO 93/02733 | 2/1993 | WIPO . |
| WO 94/24946 | 11/1994 | WIPO . |

*Primary Examiner*—Michael Buiz
*Assistant Examiner*—Kevin Truong
*Attorney, Agent, or Firm*—Morrison & Foerster, LLP

[57] ABSTRACT

This invention is a single-lumen balloon catheter and assembly having a variable stiffness shaft that allows for greater guidewire trackability and proximal pushability than previous designs. The catheter has an elongate tubular body that is made of inner and outer coaxial tubes, the inner tube being made of proximal and distal sections, the proximal section being stiffer than the distal section and the distal section being stiffer than the outer tube.

15 Claims, 1 Drawing Sheet

VARIABLE STIFFNESS BALLOON CATHETER

This is a U.S. National Phase application filed under 35 U.S.C. §371 filed on May 20, 1994, which is a continuation-in-part of U.S. application Ser. No. 08/071,284 filed on Jun. 2, 1993 now U.S. Pat. No. 5,437,632.

TECHNICAL FIELD

The invention is in the general field of surgical devices and relates specifically to an improved single lumen valved balloon catheter structure that may be used with a guidewire to access target sites through tortuous, small diameter vessels with less likelihood of kinking or other malfunction.

BACKGROUND

Catheters are hollow tubes that are inserted through the vasculature or other internal body passageways to access a particular internal body site for various diagnostic or therapeutic purposes. Angiography catheters are used to deliver radiopaque agents to a target site to enable radiographic visualization of the site. In the treatment of localized diseases such as solid tumors, catheters are used to administer chemotherapeutic agents or vasoocclusive agents. Catheters are similarly used to deliver vasoocclusive devices (e.g. coils) to site of aneurysm. Inflatable catheters, often referred to as balloon catheters, are used to dilate vessels. These catheters have a distal balloon that is inflated once the target site in a vessel is reached by the distal end of the catheter.

There are three general types of balloon catheters: a double lumen type, a valved single lumen type and a single lumen, non-movable wire type. The double lumen type has concentric inner and outer lumens with the balloon being part of the outer lumen. A guidewire is extended through the inner lumen.

In the single lumen valved type, a guidewire carries a distal valve member that can be moved by axial manipulation of the guidewire to block the distal opening of the catheter. U.S. Pat. No. 4,813,934 describes several embodiments of single lumen valved catheters. Designs in which the valve is located within the catheter lumen at the distal end of the balloon as well as designs in which the valve is located exteriorly of the lumen are shown in the patent. U.S. Pat. No. 5,171,221 describes a single lumen valved balloon catheter assembly with an exteriorly located valve wherein the guidewire is axially moveable within the lumen of the catheter and has a proximal segment with a larger diameter than the distal segment. The tip portion of the catheter tube distal segment, distal to the balloon contains a soft, elastic insert that conforms to the configuration of the valve member on the guidewire such that when the valve member is pulled back against the tip, the distal opening of the catheter is blocked and the balloon can be inflated.

The present invention involves a balloon catheter that has a variable stiffness shaft that can be better advanced into distal vessels due to better trackability and proximal pushability than prior designs.

Catheters with variable stiffness shafts have been described for insertion through tortuous small vessels such as those found in the peripheral vasculature or organs such as the brain and liver. Such catheters are commonly used in combination with a flexible torqueable guidewire. In this procedure, the guidewire is advanced through the vessel and the catheter is threaded over the guidewire. At tortuous sites in the vessel, the assembly is advanced by alternately guiding the wire through the site and then threading the catheter over the advanced segment of the wire. In order to be useful in such applications, the catheter must meet demanding physical requirements so that it does not become locked against the guidewire or become kinked as it is passed through particularly tortuous segments of the vessel. In this regard, U.S. Pat. No. 4,739,768 describes a catheter with a variable stiffness shaft specifically designed to overcome problems associated with accessing tortuous, small vessels.

The specific catheter embodiments shown in U.S. Pat. No. 4,739,768 consist of coaxial assemblies of two tubes, one of which is relatively long and stiff and defines a proximal portion of the catheter and the other of which is relatively short and flexible and defines the distal end of the catheter. The flexible distal end allows the catheter to be advanced axially over sharper and/or more frequent wire bends with less likelihood of malfunction. The patent mentions (column 5) that for longer tortuous paths, the catheter may include one or more intermediate segments having flexibilities intermediate those of the proximal and distal portions of the catheter and which, together with the distal portion, constitute 10% to 40% of the catheter length. The stated purpose of such intermediate sections is to provide greater column strength than the distal portion of the two-section embodiment and greater flexibility than the proximal section of that embodiment. The patent does not provide any specific examples of such multi-segment catheters or indicate any other purposes of a multi-segment structure.

U.S. patent application Ser. No. 07/741,775 describes a variable stiffness catheter with four segments of different flexibility comprising an outer coaxial tube and an inner coaxial tube. The inner tube has three segments of differing flexibilities, the intermediate segment being less stiff than the proximal segment and the distal segment being less stiff than the intermediate segment. The distal segment is stiffer than the outer tube which extends beyond the distal segment.

DISCLOSURE OF THE INVENTION

The present invention is a single lumen valved balloon catheter for use in combination with a guidewire. The catheter has an elongate tubular body with a proximal end and a distal end and a lumen extending between the ends for receiving the guidewire. The elongate tubular body has: (a) an inflatable balloon segment intermediate the ends and located near the distal end of the catheter; (b) an outer coaxial tube extending continuously between the proximal end and the balloon having a wall thickness of between about 0.05 to 0.13 mm and being made of a polymer having flexural modulus of about 5,000 to 30,000 psi (35,000 to 210,000 kpa); and (c) proximal and distal inner coaxial polymeric tube sections positioned contiguously in tandem within the outer tube from the proximal end to a site that is proximal to the balloon. The proximal inner section has a wall thickness of about 0.08 to 0.18 mm and is made of a polymer having a flexural modulus of about 220,000 to 260,000 psi (1,500,000 to 1,800,000 kpa). The distal section is less stiff than the proximal section but stiffer than the portion of the outer tube extending to the site that is proximal to the balloon.

In another aspect, the invention is a single lumen balloon catheter assembly. The assembly is a combination of a single lumen catheter and a flexible guidewire. The single lumen catheter has an elongate tubular body with a proximal end and a distal end and a lumen extending between the ends for receiving a guidewire. The tubular body has: (i) an inflatable balloon segment intermediate the ends located near the distal end; (ii) an outer coaxial tube that extends continuously between the proximal end and the balloon and has a wall thickness of between about 0.05 to 0.13 mm and is made of a polymer having flexural modulus of about 5,000 to 30,000 psi (35,000 to 210,000 kpa); and (iii) proximal, intermediate, and distal inner coaxial polymeric tube sections that are positioned contiguously in tandem within the outer tube from the proximal end to a site proximal the balloon. The proximal inner section has a wall thickness of about 0.08 to 0.18 mm and is made of a polymer having a flexural modulus of about 220,000 to 260,000 psi (1,500,000 to 1,800,000 kpa). The distal section is less stiff than the proximal section but stiffer than the portion of the outer tube that extends to the site that is proximal to the balloon. The flexible guidewire extends axially through the lumen beyond the open end of the catheter. The guidewire is axially moveable within the lumen of the catheter. A valve member carried on the guidewire is axially moveable by axial movement of the guidewire between a first position in which the valve member is axially spaced from the open distal end of the catheter to a second position in which the valve member is seated against and blocks the open distal end of the catheter.

DETAILED DESCRIPTION OF THE INVENTION

Figure 1:
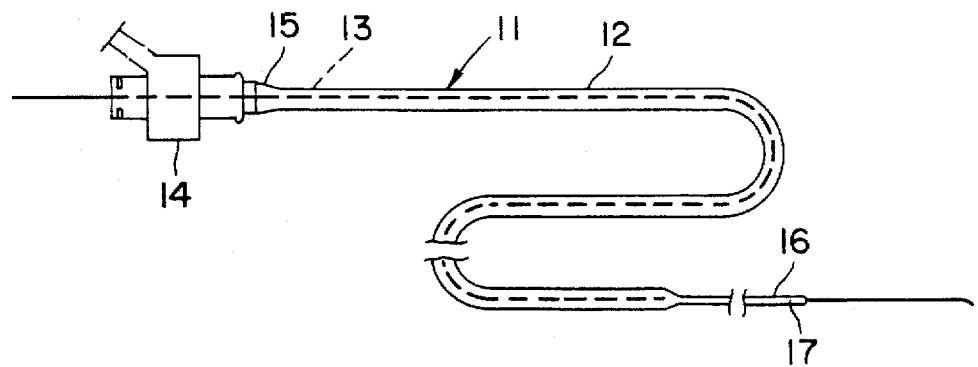
FIG. 1 is an illustration of a catheter assembly showing the catheter of the invention in combination with a guidewire.

FIG. 1 is a general view showing a catheter assembly, generally designated (11), that includes the invention catheter (12) in combination with a guidewire (13). The details of the catheter construction that distinguish it from prior structures are not shown in FIG. 1. The assembly includes a standard fitting (14) through which the guidewire is received and to which the proximal end (15) of the catheter is removably attached. As depicted, the catheter is a continuous tubular body that extends from proximal end (15) to distal end (16) and through which the guidewire extends. The distal end of the guidewire extends outwardly of the distal end (16) of the catheter. The distal region of the catheter typically carries one or more radiopaque bands (17) so that the location of the distal region of the catheter within the vessel may be visualized radiographically.

Figure 2:
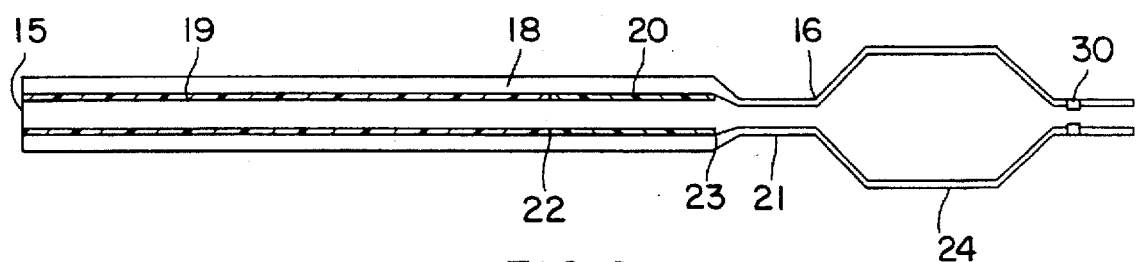
FIG. 2 is an enlarged sectional view of a portion of the catheter of the invention showing the coaxial segmented structure of the catheter.

Details of the structure of catheter (12) are shown in FIG. 2. It is composed of an outer tube (18) and two or more inner coaxial tubular sections (19) and (20). As shown, the two inner coaxial tubular sections are disposed in tandem within the outer tube and are contiguous to each other (i.e. their respective ends abut each other). The outer tube (18) extends continuously over the entire length of the catheter, which typically will be over 50 to 210 cm, more usually 60 to 150 cm. The outer diameter of tube (18) (as measured at proximal end (15)) will normally be 0.75 to 2.00 mm, preferably 0.85 to 1.30 mm. As seen in FIG. 2, the outer tube may neck down at its distal end (16) and its outer diameter at the distal end may be slightly smaller than at its proximal end. The outer tube will normally have a wall thickness of about 0.08 to 0.16 mm, preferably about 0.10 to 0.13 mm. It is made from a polymer having a flexural modulus (as measured by ASTM D-790) of about 5,000 to 30,000 psi (35,000 to 210,000 kpa), such as low density polyethylene.

The proximal inner tubular segment extends from the proximal end (15) of the catheter to junction (22). This distance will normally be 60 to 150 cm, more usually 40 to 120 cm, and preferably about 100 cm. Its wall thickness is about 0.08 to 0.18 mm, preferably about 0.10 to 0.13 mm, an it is made of a polymer having a flexural modulus of about 220,000 to 260,000 psi (1,500,000 to 1,800,000 kpa) such as polypropylene. The portion of the catheter from proximal end (15) to junction (22) is thus the stiffest portion of the catheter. The inner diameter of section (19) will normally be 0.45 to 0.75 mm.

Distal inner tubular section (20) extends from the distal end of section (19) (junction (22)) to junction (23). That distance will normally be 1 to 30 cm, more normally 1 to 20 cm, preferably about 10 cm. This section is less stiff than section (19). Accordingly, its wall thickness is less than section (19) and/or it is made of a polymer with a lower flexural modulus than the polymer forming section (19). In a preferred embodiment, it is made of a continuous length of tubing having an appropriately tapered outer diameter. Typically, the flexural modulus of the polymer forming section (20) will be 20,000 to 50,000 psi (140,000 to 350,000 kpa) more usually 30,000 to 40,000 psi (210,000 to 280,000 kpa). The wall thickness of section (20) will normally be 0.05 to 0.10 mm, preferably 0.06 to 0.09 mm. The inner diameter of section (20) is preferably substantially the same as that of section (19).

The distal section (21) of the outer coaxial tube (18) extends from the distal end of section (20) (junction (23)) to the balloon portion of the catheter. The distance from junction (23) to the balloon will usually be 1 to 20 cm, more usually 1 to 10 cm, preferably about 5 cm. The distance from proximal end (15) to junction (22) will be greater than about 50% of the entire length of catheter (12), more usually greater than about 75% of the entire catheter length. Although joint (22) is depicted as a butt joint in the drawing, the joint may be an overlap joint.

The invention catheter thus has three sections of different flexibility/stiffness and becomes increasingly flexible from segment-to-segment distally. The axial flexibility/stiffness gradient of the invention is thus more gradual than in the two-segment embodiment of U.S. Pat. No. 4,739,768 and the change in flexibility stiffness between segments is not as great as in a two segment embodiment. In particular, the inclusion of section (20) allows the distal end of the catheter to be tracked around sharp bends with less likelihood of kinking occurring at the transition between the outer tube and the distal end of the inner coaxial tubing. Further, the structure reduces the likelihood of fatigue stress failure, delamination, or other structural failure at the transition.

Figure 3:
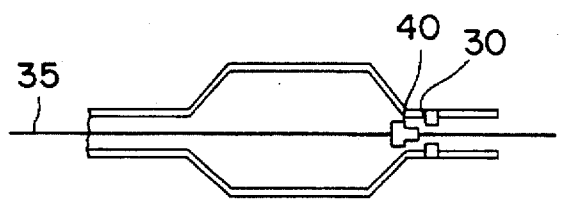
FIG. 3 is an enlarged sectional view of one embodiment of the catheter assembly wherein the plug portion of the valve assembly is distal to the balloon.
Figure 4:
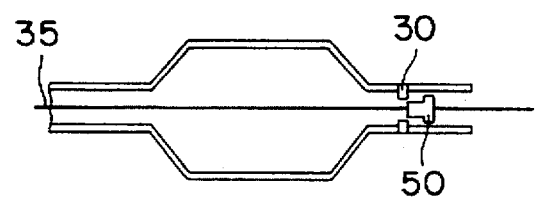
FIG. 4 is an enlarged sectional view of one embodiment of the catheter assembly wherein the plug portion of the valve assembly is proximal to the balloon.

The balloon (24) of the catheter is defined by a portion of the thin-walled distal segment of the catheter tube. In its deflated configuration, it has a diameter that approximates the diameter of the tube proximal to it. It will normally be inflatable to a maximum diameter with a range of sizes 1.5, 2.0, 2.5, 3.0, 3.5 and 4.0 mm. The valve portion (30) of the catheter assembly is preferably inserted into the portion of the balloon having relatively constant inner diameter. It is held in place by heat welding or gluing or other suitable process. The valve may be made up of a simple tube having a metal band so as to form a valve surface proximally of the metal band on the interior of the lumen and a valve surface proximally or distally of the band. The guidewire contains the valve plug, the shape of which is relatively unimportant so long as it meshes adequately with the valve surfaces formed in the valve region. FIG. 3 shows the guidewire (35) with a plug (40) that seats on the proximal side of the valve portion (30). In such a configuration, the guidewire (35) can be removed once the procedure is completed. FIG. 4 shows the guidewire (35) with a plug (50) that seats on the distal side of the valve portion (30). Accordingly, the guidewire (35) can only be withdrawn when the catheter is withdrawn.

The catheter assembly of the invention is operated in similar fashion to other valve balloon catheters. In such operation, the guidewire is advanced into the vasculature to a desired site, and the catheter body is tracked over the guidewire. The location of the guidewire and the balloon within the vessel may be determined by conventional radiology techniques. Once the balloon is at the desired site within the vessel, the catheter lumen is flushed by injecting fluid through the catheter lumen, the valve plug is seated against the distal valve surface or the proximal valve surface, depending upon the end from which the guidewire was introduced, by axially manipulating the guidewire. The valve plug blocks the distal opening of the catheter tube. The balloon is then inflated by injecting fluid through the catheter lumen. If desired, controlled distal leakage of the fluid from the catheter tip may be achieved by a slight adjustment in the tightness of the seating between the valve plug and the respective seating areas. The balloon may be deflated by withdrawing fluid from the catheter lumen.

Modifications of the above-described embodiments of the catheter and catheter assembly that are obvious to those of skill in the fields of catheter design and manufacture, materials science and related fields are intended to be within the scope of the following claims.

I claim:

1. A single lumen valved balloon catheter for use in combination with a guidewire, said catheter comprising an elongate tubular body having a proximal end a distal end and a lumen extending between said ends for receiving the guidewire, said body comprising:
   (a) an inflatable balloon segment intermediate said ends, proximate said distal end;
   (b) an outer coaxial tube extending continuously between the proximal end and the balloon; and
   (c) proximal and distal inner coaxial polymeric tube sections positioned contiguously in tandem proximal to the inflatable balloon segment and located within a portion of the outer coaxial tube; wherein a distal end of the distal inner coaxial tube section is proximal said balloon, the distal inner coaxial tube section being less stiff than the proximal inner coaxial tube section but stiffer than the portion of the outer coaxial tube extending from the distal inner coaxial tube section to the balloon.

2. The catheter of claim 1 wherein the proximal and distal inner coaxial tube sections are made of the same polymer and the wall thickness of the distal inner coaxial tube section is less than the wall thickness of the proximal inner coaxial tube section.

3. The catheter of claim 2 wherein the wall thickness of the distal inner coaxial tube section is 0.05 to 0.13 mm.

4. The catheter of claim 1 wherein the distal inner coaxial tube section has a wall thickness of 0.05 to 0.10 mm and is made of a polymer having a flexural modulus of about 30,000 to 40,000 psi (210,000 to 280,000 kpa).

5. The catheter of claim 1 wherein the outer diameter of the outer coaxial tube is 0.75 to 2.00 mm at the proximal end and 0.08 to 1.80 mm at the balloon end.

6. The catheter of claim 5 wherein the length of the outer coaxial tube is 50 to 210 cm, the length of the proximal inner coaxial tube section is 10 to 70 cm, and the length of the distal inner coaxial tube section is 5 to 20 cm.

7. The catheter of claim 1 wherein the distance from the proximal end of the catheter to the distal end of the proximal inner coaxial tube section constitutes greater than 50% of the length of the catheter.

8. The catheter of claim 1 wherein the distance from the proximal end of the catheter to a distal end of the proximal inner coaxial tube section constitutes greater than 60% of the length of the catheter.

9. The catheter of claim 1 wherein the outer coaxial tube is made of low density polyethylene, the proximal inner coaxial tube section is made of polypropylene, and the distal inner coaxial tube section is made of linear low density polyethylene.

10. The catheter of claim 1, wherein at least a portion of said outer coaxial tube has a tapered outer diameter.

11. A single lumen balloon catheter assembly comprising in combination:
   (a) a single lumen catheter comprising an elongate tubular body having a proximal end, an open distal end and a lumen extending between said ends for receiving a flexible guidewire, said body comprising:
      (i) an inflatable balloon segment intermediate said ends;
      (ii) an outer coaxial tube extending continuously between the proximal end and the balloon; and
      (iii) proximal and distal inner coaxial polymeric tube sections positioned contiguously in tandem proximal to the inflatable balloon segment and located within a portion of the outer coaxial tube; wherein a distal end of the distal inner coaxial tube section is proximal said balloon, the distal inner coaxial tube section being less stiff than the proximal inner coaxial tube section but stiffer than the portion of the outer coaxial tube extending from said distal inner coaxial tube section to the balloon;
   (b) said flexible guidewire extending axially through the lumen beyond said open distal end, said guidewire being axially moveable within the lumen; and
   (c) a valve plug carried on the guidewire and being axially moveable by axial movement of the guidewire between a first position in which the valve plug is axially spaced from the open distal end of the catheter to a second position in which the valve plug blocks the open distal end of the catheter.

12. The catheter assembly of claim 11 wherein the valve plug is carried on a distal end of the guidewire such that in order to block the open distal end of the catheter, said guidewire is pulled, urging said valve plug towards said open distal end.

13. The catheter assembly of claim 11 wherein the valve plug is carried on the distal end of the guidewire such that in order block the open distal end of the catheter, said guidewire is pushed, urging said valve plug towards said open distal end.

14. The catheter of claim 11 further comprising a valve surface adapted to mate with said valve plug, said valve surface positioned within a portion of the balloon having relatively constant inner diameter.

15. The catheter of claim 14 wherein the valve surface consists of a metal band inserted into a portion of the balloon having relatively constant inner diameter.

* * * * *